United States Patent
Eletreby et al.

(10) Patent No.: US 9,501,615 B2
(45) Date of Patent: *Nov. 22, 2016

(54) SYSTEM AND METHOD FOR MANAGEMENT OF DRUG LABELING INFORMATION

(71) Applicant: CERNER INNOVATION, INC., Kansas City, KS (US)

(72) Inventors: Magdy A. Eletreby, Dana Point, CA (US); Mohamed N. Eletreby, Huntington Beach, CA (US)

(73) Assignee: Cerner Innovation, Inc., Kansas City, KS (US)

(*) Notice: Subject to any disclaimer, the term of this patent is extended or adjusted under 35 U.S.C. 154(b) by 2 days.

This patent is subject to a terminal disclaimer.

(21) Appl. No.: 14/572,373

(22) Filed: Dec. 16, 2014

(65) Prior Publication Data

US 2015/0169825 A1 Jun. 18, 2015

Related U.S. Application Data

(63) Continuation of application No. 10/951,572, filed on Sep. 28, 2004, now Pat. No. 8,918,432.

(60) Provisional application No. 60/589,117, filed on Jul. 19, 2004.

(51) Int. Cl.
| | | |
|---|---|---|
| *G06F 17/30* | (2006.01) | |
| *G06F 19/00* | (2011.01) | |
| *G06Q 99/00* | (2006.01) | |

(52) U.S. Cl.
CPC ......... *G06F 19/32* (2013.01); *G06F 17/30876* (2013.01); *G06F 19/326* (2013.01); *G06Q 99/00* (2013.01); *G06F 19/3456* (2013.01)

(58) Field of Classification Search
CPC ............ G06F 17/30876; G06F 19/32; G06F 19/326; G06F 19/3456; G06Q 99/00
USPC ...... 707/802, 607; 705/2; 700/231, 235, 236
See application file for complete search history.

(56) References Cited

U.S. PATENT DOCUMENTS 6,068,156 A * 5/2000 Liff ..................... G06F 19/3462
  221/129
7,630,908 B1 * 12/2009 Amrien ................. G06F 19/322
  235/487

(Continued)

OTHER PUBLICATIONS

Smith, Neil V., et al., "Taking the Package Insert into the Electronic Age", Drug Information Journal, vol. 36, No. 2, Apr. 2002, pp. 429-434.*

*Primary Examiner* — Robert Stevens
(74) *Attorney, Agent, or Firm* — Shook, Hardy & Bacon L.L.P.

(57) ABSTRACT

A system for managing drug labeling information includes a repository comprising a network accessible database, the repository having an upload portion and a download portion, the repository being accessible to a plurality of users via client computers coupled to a wide area network. The repository includes drug labeling information on a plurality of drugs stored therein. The upload portion of the repository is accessible by a first set of users while the download portion of the repository is accessible by a second set of users. In one preferred aspect of the invention, drug manufactures are able to upload new or revised PDF files containing drug labeling information. The new or revised PDF files are then available for download by pharmacists or other authorized users.

18 Claims, 5 Drawing Sheets (56) References Cited

U.S. PATENT DOCUMENTS

2002/0042725 A1* 4/2002 Mayaud .............. G06F 19/3456
705/2
2002/0077857 A1* 6/2002 Seelinger ............... G06Q 50/22
705/2
2002/0087554 A1* 7/2002 Seelinger .............. G06F 19/326
2003/0055683 A1* 3/2003 Gibson ................. G06F 19/326
705/2
2004/0215486 A1* 10/2004 Braverman ......... G06F 19/3462
705/2

* cited by examiner

Electronic Product Labeling

| NDC | Brand Name | Generic Name | Manufacturer |
|---|---|---|---|
| 0018619804 | PULMICORT RESPULES | Budesonide Inhalation Suspension | ASTRAZENECA |
| 00186198904 | PULMICORT RESPULES | Budesonide Inhalation Suspension | ASTRAZENECA |
| 00186091542 | PULMICORT TURBOHALER | Budesonide Inhalation Powder | ASTRAZENECA |

- Home
- Configuration Assistant
- Change Password
- About Us
- Links
- Help
- Participating Manufacturers
- Contact Us
- Logout

SEARCH BY:
- ⦿ Brand/Generic Name/NDC
- ○ Manufacturer

[Submit] — 205

Keep Current
Update Notifications!
Please enter your email address to be notified of updates:

[Subscribe!] — 215
Privacy Policy

Get Acrobat Reader
For Netscape Users, please click here

This site is hosted and maintained by *Etreby Computer Company*

SYSTEM AND METHOD FOR MANAGEMENT OF DRUG LABELING INFORMATION

CROSS-REFERENCE TO RELATED APPLICATIONS

This application is a continuation of U.S. patent application Ser. No. 10/951,572, filed Sep. 28, 2004, entitled "System and Method for Management of Drug Labeling Information," which claims priority to U.S. Provisional Patent Application Ser. No. 60/589,117, filed Jul. 19, 2004, entitled "Internet Portal-Based System For Management Of Drug Labeling Documentation." The entirety of the aforementioned applications are incorporated by reference herein in their entireties.

TECHNICAL FIELD

The field of the invention generally relates to systems and methods used to manage documents using a wide area network (WAN) such as the Internet. More specifically, the field of the invention relates to systems and methods used to manage prescribing information for drugs and other medicines.

BACKGROUND OF THE INVENTION

Currently, rules established by the U.S. Food and Drug Administration (FDA) require that product use labeling information presented in document form on printed paper be dispensed on or within the package from which the drug is to be dispensed. See 21 C.F.R. §201.110 (c)(1). One goal of this regulation is to ensure that the pharmacist dispensing the drug or medicine has access to the full prescribing information. Because the paper document containing the labeling information is physically attached (or inserted into) the drug packaging, the prescribing information has become referred to as a "package insert."

A number of steps are required to produce and place the prescribing information with each drug container or bottle. While the process varies to a certain extent with different drug manufacturers, the following steps are generally required to produce these package inserts. First, text (as well as any illustrations or graphical features) for the prescribing information is finalized within the drug manufacturing company. This first step often requires consultation with and ultimate approval by the FDA. The text and any other information are then finalized using desktop publishing software. The type is set using the desktop publishing software and proofs are printed for review. Once the proofs are read and approved, they are sent to a printer for printing. The printed labeling is then folded and warehoused until needed on the manufacturing line. Finally, the labeling (i.e., package insert) is attached or inserted into product containers and bottles.

Unfortunately, there are a number of disadvantages with the current paper-based package inserts. First, a significant amount of expense both in material costs as well as labor is expended in printing up and placing the package inserts into each drug package. These costs include the personnel specific to labeling production and printing, costs of paper and printing, packaging machines which fold and attach or insert the labeling, costs associated with warehousing the package inserts, quality assurance costs, as well as waste labeling due to changes and/or revisions in package inserts.

The above-described current practice of using individual package inserts also suffers from the limitation that it may take a significant amount of time for a new label to be associated with a current prescribed drug or medicine. For example, the above-described process may take several weeks for a new product. Even to replace or modify a package insert for a currently marketed product may take a few weeks due to the need to coordinate all these steps. Drug company policies such as "use up and replace" when labeling changes are minor further delay access to the new labeling information.

In addition, in the current package insert-based system, pharmacists or other health care professionals may not have access to the most current information for a particular drug. Typically, the time from manufacturing to dispensing at a pharmacy varies greatly depending on the particular drug. For frequently prescribed and dispensed products which are manufactured and dispensed immediately, this time period may be as little as two weeks. However, for infrequently prescribed and dispensed products that may be manufactured only once a year, the labeling may well be over a year old before the product even reaches the pharmacy. Similarly, the time from when a labeling change is made to the time when a physician receives the updated information may vary greatly. For physicians that prescribe high volumes of a drug, a sales representative may visit physicians on a monthly basis. Still other physicians may not be visited at all by a sales representative. Some physicians may prefer, for example, to review periodic published third-party compilations for current prescribing information. Other physicians may be notified by advertisements or promotional materials generated by the drug manufacturing company.

There are problems, however, with the timeliness of these notifications. Third-party publications and/or periodicals may be as much as one year out of date. Company-produced materials are more current, but these may contain prescribing information that has been changed since the time of printing.

The paper-based package inserts often have poor readability. Due to the expanding amount of information required in the product labeling, the size of the package insert is increasing while the size of the font used has been progressively decreasing. Many package inserts are oversized or long "scrolls" which are hard to handle and read.

There thus is a need for an alternative system and method of providing pharmacists or other health professionals with up to-date and readable prescription information for drugs and medicines.

BRIEF SUMMARY OF THE INVENTION

In one aspect of the invention, a system for managing drug labeling information includes a repository including a network accessible database, the repository having an upload portion and a download portion, the repository being accessible to a plurality of users via client computers coupled to a wide area network such as the Internet. The repository includes drug labeling information on a plurality of drugs stored therein. The upload portion of the repository is accessible by a first set of users (e.g., drug manufacturers), while the download portion of the repository is accessible by a second set of users (e.g., pharmacists).

In another aspect of the invention, a method of providing drug labeling information prepared by pharmaceutical manufacturers to pharmacists includes the steps of providing a repository comprising a network accessible database. The repository has an upload portion and a download portion via client computers coupled to a wide area network. The repository includes drug labeling information on a plurality of drugs stored therein. The upload portion of the repository is accessible by the plurality of drug manufacturers while the download portion of the repository is accessible by pharmacist. New or revised drug labeling information from a drug manufacturer is uploaded to the repository. Next, the network accessible database is then updated on a real time or periodic basis so as to identify the new or revised drug labeling information.

In another aspect of the invention, a method of providing drug labeling information prepared by pharmaceutical manufacturers to pharmacists includes the steps of transmitting a PDF document containing drug labeling information from a first client computer to a remote server, storing the PDF document in a searchable database on the remote server, querying the searchable database by one of manufacturer name, brand name, generic name, and NDC number, and transmitting a PDF document identified in the querying step to a second client computer remote from the server.

It is an object of the invention to provide a system and method for delivering up-to-date and timely drug labeling information to selected users such as, for example, pharmacists without using paper-based labels. Other objects of the invention are set forth below.

DETAILED DESCRIPTION OF THE INVENTION

Figure 1:
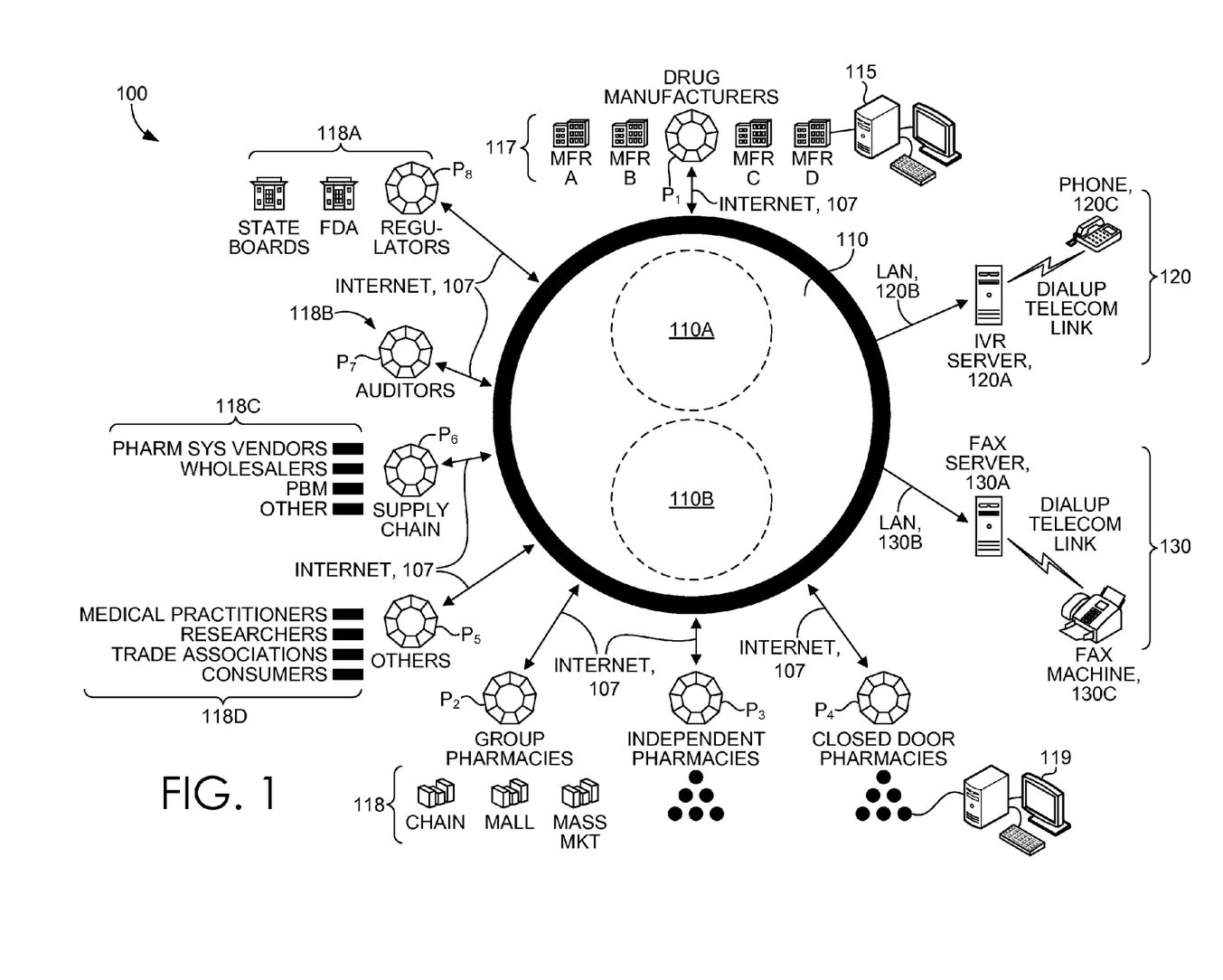
FIG. 1 schematically illustrates a system for managing drug labeling information stored in electronic form.
Figure 5:
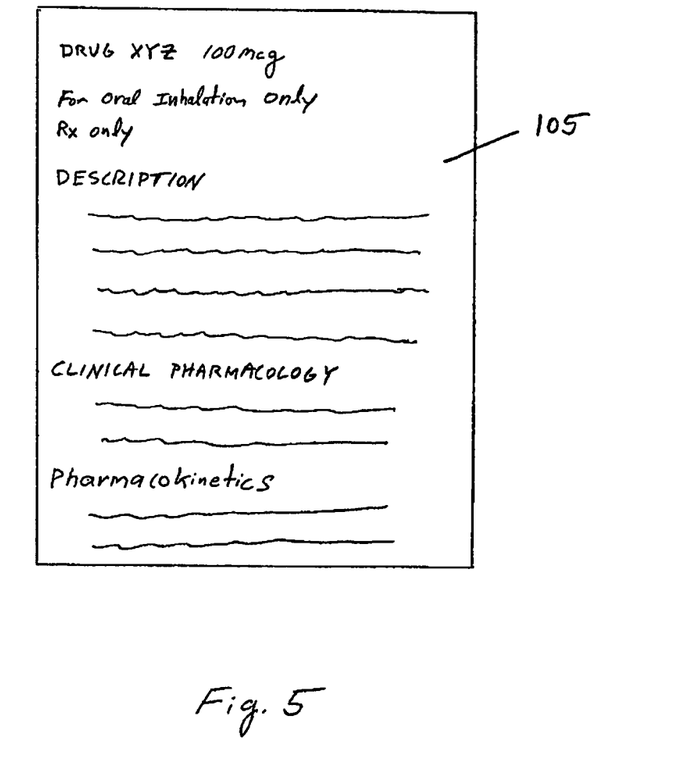
FIG. 5 graphically illustrates a first page of a PDF document containing drug labeling information.

FIG. 1 schematically illustrates a system 100 for managing drug labeling information 105 (as shown in FIG. 5) according to a preferred aspect of the invention. The system 100 includes a repository 110, which in a preferred embodiment of the invention, is a network accessible database that allows for both the storage and retrieval of drug labeling information 105 on a plurality of drugs and/or medicines. The repository 110 is accessible via a Wide Area Network (WAN) 107 such as, for example, the Internet. In a preferred aspect of the invention, the repository 110 includes an upload portion 110(a) and a download portion 110(b). The upload portion 110(a) is preferably accessible to a first set of users 117 via client computers 115 connected to the WAN. In one preferred aspect of the invention, the first set of users 117 which can access the upload portion 110(a) of the repository 110, comprises authorized users from drug manufacturers (drug manufacturers A, B, C, and D are shown in FIG. 1). The download portion 110(b) is preferably accessible to a second set of users 118 also via client computers 119 connected to the WAN. In a preferred aspect of the invention, the second set of users includes authorized pharmacists. This may include, for example, group pharmacies, independent pharmacies, and closed door pharmacies. The second set of users 118 may also include authorized users from regulatory agencies 118(a), such as the Food and Drug Administration, state health boards, auditors 118(b), wholesalers, and supply chain entities 118(c), such as pharmacy system vendors, wholesalers, pharmacy benefits managers, as well as others 118(d), such as medical practitioners, researchers, trade groups, or even consumers.

The database for the repository 110 is preferably located in a computer such as, for example, a server or the like. The database is preferably managed by database management software such as MICROSOFT SQL SERVER 2000. In addition, the database software advantageously offers versioning, security, as well as history and audit services (to ensure that the correct drug labeling information repository 110 is accessible to the correct users). History and audit services (e.g., a revision tracker) allow certain users to monitor the uploading and/or downloading of new or revised PDF (Portable Document Format) files. This feature may be accessed by drug manufacturers, regulatory agencies, or others who need to know the details (such as update time, user ID, track changes, version, etc.) about an added or altered record contained within the database.

Preferably, the repository 110 is accessible via a WAN 107, such as the Internet, by using a web-based portal system. In this regard, a user is able to access the particular portion of the repository 110 by using Internet browsing software located on a client computer (115 or 119). In one aspect of the invention, a first portal $P_1$ is provided for a first set of users such as, for example, drug manufacturers. A second portal $P_2$ is then provided for a second set of users such as, for example, pharmacists. In one optional aspect of the invention, as is shown in FIG. 1, a separate portal ($P_1$-$P_8$) for each type of user may be employed. In an alternative configuration, all those users which only have access to the download portion 110(b) of the repository 110 may access the database via a single portal (e.g., $P_2$), while users which have access to the upload portion 110(a) of the repository 110 may access the database via another portal (e.g., $P_1$). In still an alternative configuration, a single portal (e.g., one of $P_1$-$P_8$) may be used for both the first and second set of users. In this embodiment, user identification information (such as a login ID) may direct the particular user to either the upload portion 110(a) or download portion 110(b) (or both) of the repository 110.

Still referring to FIG. 1, the repository 110 is preferably linked to an Interactive Voice Response (IVR) system 120 which may include an IVR server 120(a) which is coupled to the repository 110 via a Local Area Network (LAN) 120(b). The IVR server 120(a) is able to receive information from users based upon keypad entries made on the touch-tone dial pad of a phone 120(c). Menu driven software loaded onto the IVR server 120(a) permits users to search for drug labeling information 105 based on manufacturer name, brand name, generic name, and national drug code (NDC) number. The IVR server 120(a) can then send the requested drug labeling information 105 to the user either telephonically, via e-mail, or facsimile (described below).

In a preferred aspect of the invention, the repository 110 is also linked to a facsimile delivery system 130, which preferably includes a dedicated facsimile server 130(a) which is coupled to the repository via a LAN 130(b). The facsimile server 130(a) is able to deliver facsimile copies of drug labeling information 105 to a facsimile machine 130(c) (or other device such as a computer capable of receiving facsimile copies) using a standard dial-up telecommunications link. Preferably, the facsimile server 130(a) is a dedicated Right FAX IVR server which is connected to the LAN 130(b) using a standard network interface card. In an alternative aspect of the invention, the IVR system 120 and facsimile delivery system 130 may be combined into a single integrated server.

Figure 2:
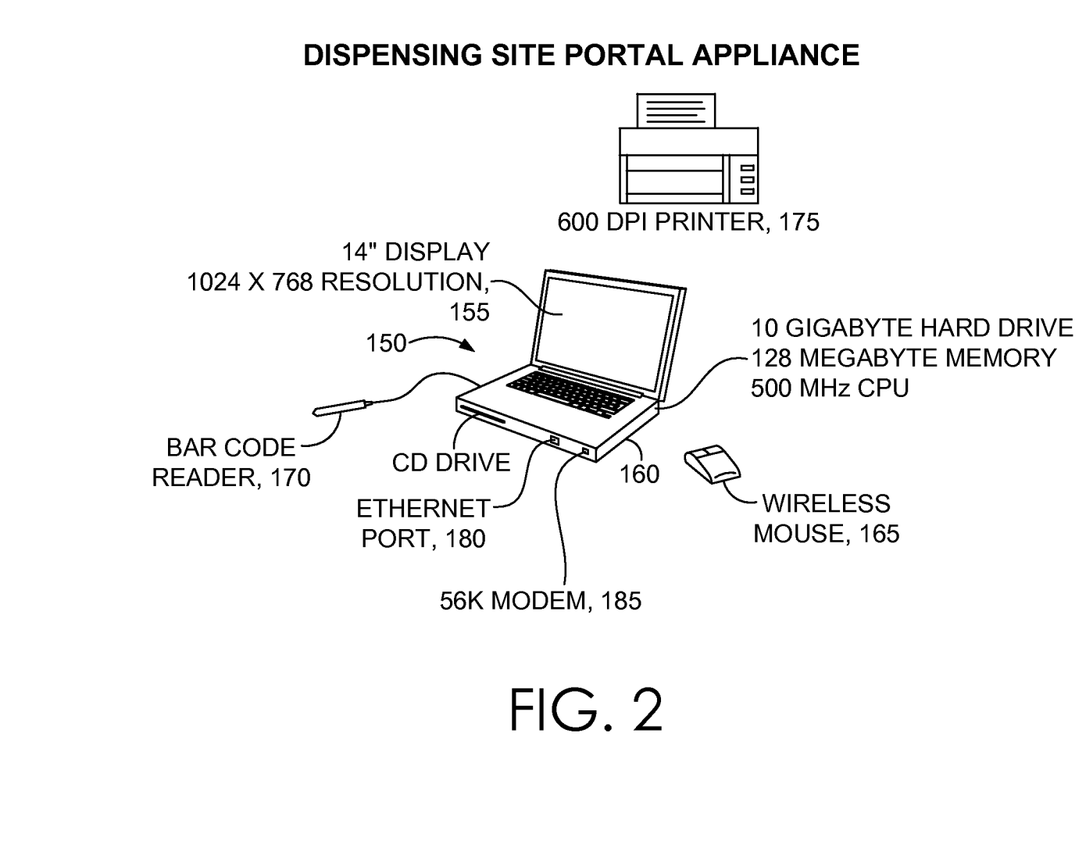
FIG. 2 illustrates a computer used to access the repository containing the drug labeling information.

FIG. 2 illustrates a typical client computer 150 used by the second set of users (e.g., computers located at pharmacist dispensing sites) described above. The client computer 150 preferably includes a display 155, keyboard 160, mouse 165, bar code reader 170, and printer 175. The computer 150 preferably includes a hard drive having at least 10 GB capacity as well as 500 MHz CPU with 128 Mbytes of memory. A wireless mouse 165 is preferred because it easier for the pharmacist (or other user) to navigate. The client computer 150 also preferably includes an Ethernet card and port 180 which can be connected via cable or wireless connection to a broadband modem (not shown) such as a cable or DSL modem. Alternatively, or in addition to, the computer 150 may include a dial-up modem 185 (e.g., 56K modem) which can access the Internet via a dial-up connection.

Preferably, the computer 150 has a small footprint and has a minimal impact on the dispensing site workspace and workflow. The computer 150 (such as a laptop computer) may even be mounted on a wall to mitigate disruption of existing counter and workspaces. The bar code reader 170 or wand enables users to easily input requested drug labeling information 105 by simply scanning the bottle or package bearing the bar code. Of course, user input can also be provided by a keyboard 160 connected to the client computer 150. In the context of a web accessible portal system, the bar code reader 170 can be used to populate a search field with drug identification information stored in the bar code label. In this aspect of the invention, the user simply places the cursor into the search field (described in more detail below) of the web-accessible portal system and scans the bar code on the package or bottle. The drug identification information (i.e., drug name or NDC number) is automatically input into the search field.

Figure 3:
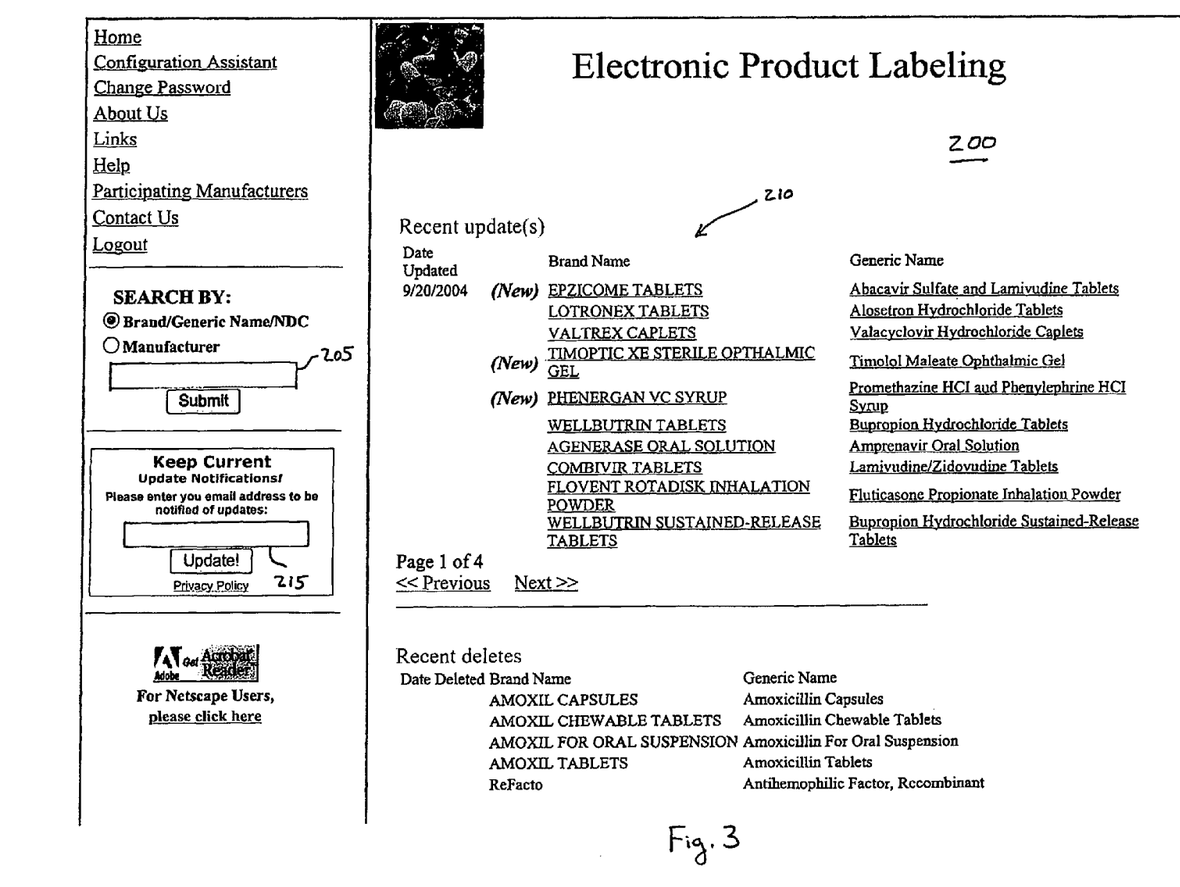
FIG. 3 illustrates a typical screen shot of a web-based portal used to obtain drug labeling information on one or more drugs.

FIG. 3 illustrates a typical screen shot 200 of a web-based portal (e.g., P₂) which is used to obtain drug labeling information 105 on one or more drugs. Prior to obtaining access to the portal P₂, the user is prompted to enter a login ID and password. In this regard, only certain users are able to access the repository 110. For example, for the portal used by drug manufacturers P₁, only authorized users from the drug manufacturers would be able to login and access the upload portion 110(a) of the repository database. As seen in FIG. 3, the web page includes a search field 205 which is used by the user to search the database of the repository 110. The user can search using brand name of the drug, the generic name of the drug, or the NDC number. Alternatively, the user can search by drug manufacturer. In this second mode, a user first types in the drug manufacturer (e.g., Pfizer). A list of all the drugs manufactured by Pfizer then appears to the user on the display 155. Each listed drug is hyperlinked to the corresponding PDF file containing the drug labeling information 105. In this regard, the user is able to drill down within the database until the correct drug (or dosage or form of a particular drug) is found.

As stated above, text can be entered into the search field 205 by using either a computer keyboard 160 and/or bar code reader 170. For the later device, the user simply places the cursor within the search field 205 and scans the bar code located on the bottle or package with the bar code reader 170. The database of the repository 110 can be searched by using any number of search methods including, for example, full text searching, natural language searching, context-based searching, parametric searching, or pre-defined searching.

Still referring to FIG. 3, the web page includes a notification field 210 which is used to notify the user of recent updates to the repository 110. This may include new drug labeling information 105 or updated drug labeling information 105 of a drug already contained within the repository 110 database (or even a deleted record). Preferably, the notification field 210 is updated within about 12 hours of receiving the new or updated PDF file. In one aspect of the invention, the notification field 210 is updated on a real time basis after a file has been uploaded into the repository 110. After a pre-determined amount of time, record(s) displayed in the notification field 210 are removed.

In one aspect of the invention, a user is also able to enter an e-mail address to get updates sent to him/her via electronic mail. FIG. 3 illustrates an update field 215 in which a user can specify an e-mail address where updates should be sent. When the repository 110 is updated, an e-mail is automatically generated and sent to the user at the input e-mail address notifying the user of the particular update(s). This update may be sent immediately after drug labeling information 105 is uploaded or updated. Alternatively, updates may be sent out on a periodic basis (e.g., once or twice a day). In another aspect of the invention, a facsimile number may be provided which will be used to delivery facsimile updates. Preferably, the update information is sent out on a periodic or real time basis. With respect to real time updates, as soon as a drug manufacturer uploads new or revised drug labeling information 105 to the repository 110, the user is immediately notified of the update.

In another aspect of the invention, an update notification agent may be used to inform user(s) of updates to the repository 110 database. The update notification agent is a software program downloaded to the client computer (115 or 119) preferably from a remote server. The update notification agent preferably runs in the background of the client computer (115 or 119) and periodically checks with the server or other computer containing the repository 110 database to see if there are any new updates. These updates may include, for example, new, changed, or even deleted files containing drug labeling information 105.

When the update notification agent determines that a file has been added, changed, or deleted, the user on the client computer (115 or 119) is notified by a pop-up window which is preferably located in the lower right-hand corner of the display or monitor 155. Optionally, additional notifications via e-mail and/or facsimile will be delivered to the user at the same time.

The pop-up window preferably includes a hyper texted link to the appropriate portal (e.g., P₁-P₈). If the user (115 or 119) is already logged in, the user is immediately directed to the web page where updates are shown (i.e., FIG. 3). If the user (115 or 119) is not yet logged in, the user is immediately directed to the login web page.

Figure 4:
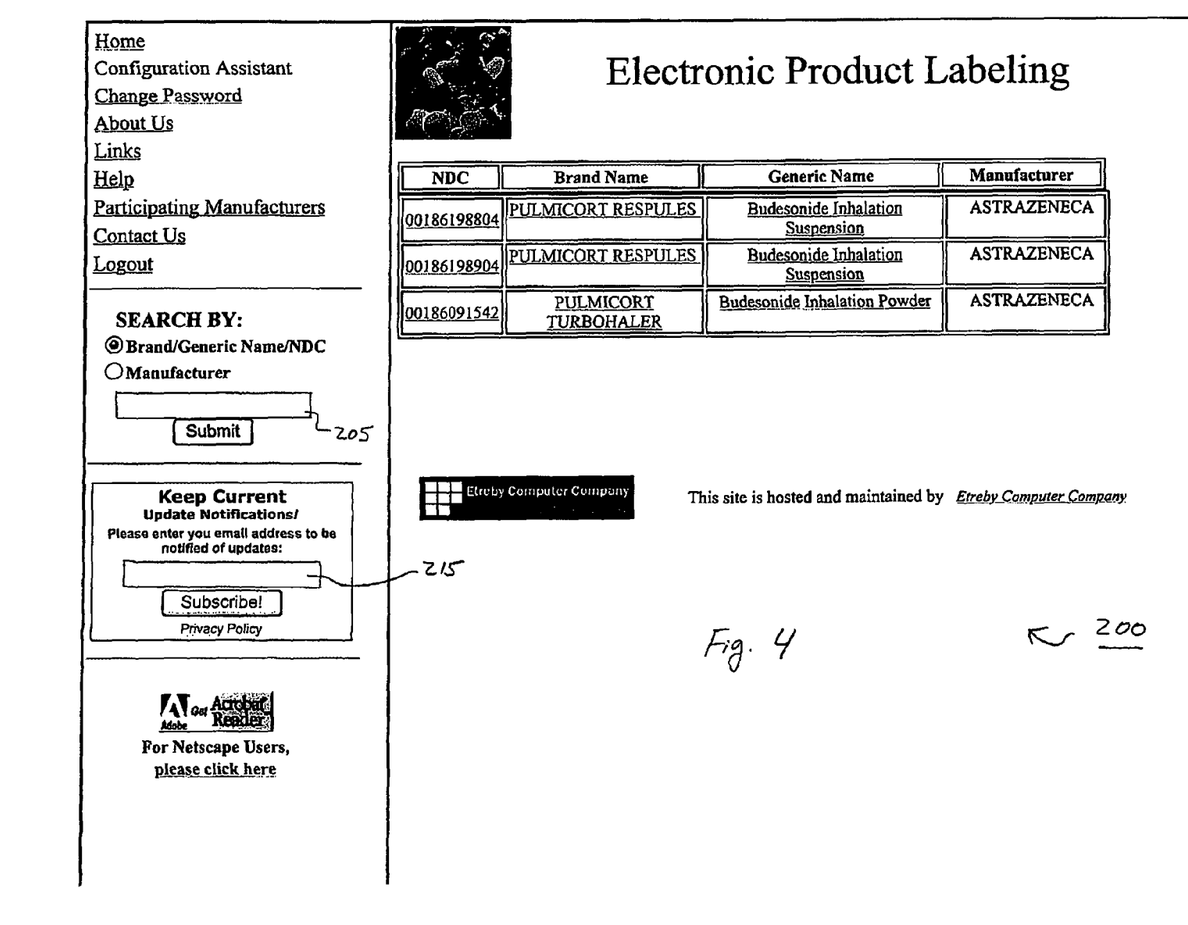
FIG. 4 illustrates the search results for an example drug: PULMICORT.

FIG. 4 illustrates the typical search results for an example drug, in this case, PULMICORT was typed into the search field 205. The results are displayed in table format showing NDC number, brand name, generic name, and manufacturer. In this particular example, there are three results or hits based on the search for "PULMICORT." These include two types of PULMICORT respules and the PULMICORT TURBOINHALER. Preferably, three of the table fields (i.e., NDC number, brand name, and generic name) are hyperlinked to the correct PDF file containing the drug labeling information 105. By clicking on the hyperlink, a PDF reader application is launched (if not already running) on the computer (e.g., computer 119) and loads the appropriate file stored within the database of the repository 110. Preferably, the reader application is ADOBE ACROBAT reader software. The reader application may even be incorporated into the web browser program itself.

In alternative embodiments, additional information pertaining to the drug may be included in the database of the repository 110. For example, photographs or other pictures of the drug (i.e., picture showing distinguishing features of pill such as, for example, markings, geometric shape, color, size) may be included. These may advantageously be presented to the user in response to a search request. Using the PULMICORT search described above, the table would include an additional field which the user could then click on to obtain a picture or photo of the drug (in this case an inhaler device). This particular feature may aid the pharmacist or other health care professional recognize or identify the particular drug.

FIG. 5 graphically illustrates a first page of a PDF document loaded after clicking on one of the three hypertext linked fields (NDC number, brand name, or generic name). The drug labeling information 105 is then displayed to the user on the display 155 or other monitor. Typically, the drug labeling information 105 includes, for example, a description of the drug, clinical pharmacology of the drug, pharmacokinetic information, pharmacodynamics, results from clinical studies, indications and usage, contraindications, warnings, precautions, drug interaction information, information on carcinogenesis, mutagenesis, and fertility, adverse reaction information, overdose information, dosage and administration information, and supply information (how the drug is supplied and/or delivered).

With respect to uploading of PDF files containing drug labeling information 105, a first set of users 117 (e.g., authorized persons from drug manufacturers) are granted access to the upload portion 110(a) of the repository 110 (or a single user 117). An authorized user 117 uploads the PDF file via computer workstation 115 which is coupled to a WAN. In one aspect of the invention, the user 117 uses Internet browser software loaded on the computer 115 to connect to portal $P_1$. The portal $P_1$ may include input fields, menus, tabs, and/or browsing features which allow the user 117 to upload a particular PDF file containing drug labeling information 105. For example, the user 117 may click a button allowing the user to browse 117 a hard drive or other storage medium connected to the computer 115 to search for the PDF file of interest. The individual PDF file can then be selected and transferred to the repository 110. In an alternative embodiment, specialized client-based software running on one or more computer 115 are used to manage and transmit new or updated PDF files. In this regard, the portal $P_1$ and Internet browsing software may be eliminated. In addition, other file transfer methods such as FTP transfers may be used to transmit new or updated PDF files containing drug labeling information. Access to the upload portion 110(a) of the repository 110 to a first set of user(s) 117 may be accomplished by use of specially assigned login IDs and/or passwords.

While embodiments of the present invention have been shown and described, various modifications may be made without departing from the scope of the present invention. The invention, therefore, should not be limited, except to the following claims, and their equivalents.

What is claimed is:

1. A computer-implemented method of providing electronic package inserts prepared by pharmaceutical manufacturers to pharmacists comprising the steps of:
   providing a computerized repository comprising a network accessible database, the computerized repository having an upload portion and a download portion, the computerized repository being accessible to a plurality of drug manufacturers via client computers coupled to a wide area network, the computerized repository including electronic package inserts for a plurality of drugs stored therein, the upload portion of the computerized repository being accessible by the plurality of drug manufacturers while the download portion of the computerized repository is accessible by pharmacists;
   uploading one or more new or revised electronic package inserts from a drug manufacturer to the computerized repository;
   updating the network accessible database on a real time or periodic basis so as to identify the one or more new or revised electronic package inserts, the one or more new or revised electronic package inserts for each drug comprising a description of the drug, clinical pharmacology of the drug, indications and usage of the drug, contraindications of the drug, or warnings; and
   providing an alert, for one or more pharmacists, of any new or revised electronic package insert via a notification field that corresponds with an indication of a drug that is hyperlinked to an electronic document containing the new or revised electronic package insert for the drug.

2. The computer-implemented method of claim 1, wherein providing the alert of any new or revised package insert comprises displaying said information on a web site portal accessible by pharmacists.

3. The computer-implemented method of claim 1, wherein providing the alert of any new or revised package insert comprises transmitting said alert via electronic mail.

4. The computer-implemented method of claim 1, wherein providing the alert of any new or revised package insert comprises transmitting said information to one or more client devices associated with one or more pharmacists.

5. The computer-implemented method of claim 1, further comprising providing new or revised package inserts to a client computer located at a pharmacist dispensing location.

6. The computer-implemented method of claim 1, further comprising receiving a search query comprising a manufacturer name, a brand name, a generic name, or a national drug code (NDC) number transmitted from a client computer located at a pharmacist dispensing location.

7. A system for managing drug labeling information comprising:
   a repository comprising a network accessible database, the repository having an upload portion and a download portion and being accessible to a plurality of drug manufacturers via client computers coupled to a wide area network, the repository including electronic package inserts for a plurality of drugs stored therein, the upload portion of the repository being accessible by the plurality of drug manufacturers while the download portion of the repository is accessible by pharmacists; and
   a computer server comprising at least one processor, wherein the computer server is configured to;

receive one or more new or revised electronic package inserts from a drug manufacturer for storage in the repository, update the network accessible database on a real time or periodic basis so as to identify the one or more new or revised electronic package inserts, the one or more new or revised electronic package inserts for each drug comprising a description of the drug, clinical pharmacology of the drug, indications and usage of the drug, contraindications of the drug, or warnings, and initiate an alert, for one or more pharmacists, of any new or revised electronic package insert via a notification field that corresponds with an indication of a drug that is hyperlinked to an electronic document containing the new or revised electronic package insert for the drug.

8. The system of claim 7, wherein initiating the alert of any new or revised package insert comprises displaying said information on a web site portal accessible by pharmacists.

9. The system of claim 7, wherein initiating the alert of any new or revised package insert comprises transmitting said alert via electronic mail.

10. The system of claim 7, wherein initiating the alert of any new or revised package insert comprises transmitting said information to one or more client devices associated with one or more pharmacists.

11. The system of claim 7, further comprising providing new or revised package inserts to a client computer located at a pharmacist dispensing location.

12. The system of claim 7, further comprising receiving a search query comprising a manufacturer name, a brand name, a generic name, or a national drug code (NDC) number transmitted from a client computer located at a pharmacist dispensing location.

13. One or more computer hardware storage devices having computer-executable instructions embodied thereon that, when executed, facilitate a method of providing electronic package inserts, the method comprising:

providing a computerized repository comprising a network accessible database, the computerized repository having an upload portion and a download portion, the computerized repository being accessible to a plurality of drug manufacturers via client computers coupled to a wide area network, the computerized repository including electronic package inserts for a plurality of drugs stored therein, the upload portion of the computerized repository being accessible by the plurality of drug manufacturers while the download portion of the computerized repository is accessible by pharmacists;

uploading one or more new or revised electronic package inserts from a drug manufacturer to the computerized repository;

updating the network accessible database on a real time or periodic basis so as to identify the one or more new or revised electronic package inserts, the one or more new or revised electronic package inserts for each drug comprising a description of the drug, clinical pharmacology of the drug, indications and usage of the drug, contraindications of the drug, or warnings; and providing an alert, for one or more pharmacists, of any new or revised electronic package insert via a notification field that corresponds with an indication of a drug that is hyperlinked to an electronic document containing the new or revised electronic package insert for the drug.

14. The devices of claim 13, wherein providing the alert of any new or revised package insert comprises displaying said information on a web site portal accessible by pharmacists.

15. The devices of claim 13, wherein providing the alert of any new or revised package insert comprises transmitting said alert via electronic mail.

16. The devices of claim 13, wherein providing the alert of any new or revised package insert comprises transmitting said information to one or more client devices associated with one or more pharmacists.

17. The devices of claim 13, further comprising providing new or revised package inserts to a client computer located at a pharmacist dispensing location.

18. The devices of claim 13, further comprising receiving a search query comprising a manufacturer name, a brand name, a generic name, or a national drug code (NDC) number transmitted from a client computer located at a pharmacist dispensing location.

* * * * *